(12) United States Patent
Kauker et al.

(10) Patent No.: US 8,226,677 B2
(45) Date of Patent: Jul. 24, 2012

(54) SENSING ARRANGEMENT FOR CONTROL OF POWERED CUTTING DEVICE

(75) Inventors: Barry Kauker, Soquel, CA (US); Ryon Dierck, Kernville, CA (US); Reid Cover, Mountain View, CA (US)

(73) Assignee: Stryker Corporation, Kalamazoo, MI (US)

( * ) Notice: Subject to any disclaimer, the term of this patent is extended or adjusted under 35 U.S.C. 154(b) by 317 days.

(21) Appl. No.: 12/589,317

(22) Filed: Oct. 21, 2009

(65) Prior Publication Data

US 2010/0100112 A1    Apr. 22, 2010

Related U.S. Application Data

(60) Provisional application No. 61/196,957, filed on Oct. 22, 2008.

(51) Int. Cl.
*A61B 17/32* (2006.01)

(52) U.S. Cl. ........................................ 606/180

(58) Field of Classification Search .......... 606/170–180, 606/200; 604/19, 22, 540–544; 210/739, 210/741
See application file for complete search history.

(56) References Cited

U.S. PATENT DOCUMENTS

| 5,270,622 | A | | 12/1993 | Krause |
| 5,602,449 | A | | 2/1997 | Krause et al. |
| 5,643,304 | A | * | 7/1997 | Schechter et al. ............ 606/171 |
| 5,669,921 | A | | 9/1997 | Berman et al. |
| 5,733,298 | A | * | 3/1998 | Berman et al. ................ 606/167 |
| 5,810,858 | A | | 9/1998 | Berman et al. |
| 2001/0031976 | A1 | * | 10/2001 | Lobdell ......................... 606/171 |
| 2003/0135151 | A1 | | 7/2003 | Deng |
| 2005/0267504 | A1 | * | 12/2005 | Boukhny et al. .............. 606/171 |
| 2007/0016152 | A1 | * | 1/2007 | Karpowicz et al. ........... 604/326 |

\* cited by examiner

*Primary Examiner* — Ryan Severson
*Assistant Examiner* — Anh Dang
(74) *Attorney, Agent, or Firm* — Flynn, Thiel, Boutell & Tanis, P.C.

(57) ABSTRACT

Sensing arrangements for a handpiece sense suction pressure or fluid flow within a suction path to determine the position of a movable cutting element relative to a fixed cutting element of a cutting accessory. A controller calculates actual speed of the movable cutting element from measured pressure or measured fluid flow. The cutting elements have openings that, when aligned, form a window. The controller controls power to a motor that drives the cutting element. When the handpiece is deactivated, the controller stops the movable cutting element at a predetermined position to close or partially close the window. The controller controls the cutting speed in view of joint pressure combined with suction pressure, or in view of fluid flow through the suction path, to maintain an optimal fluid flow rate that enhances the cutting action of the cutting accessory. Pressure or flow sensors may detect a clog in the suction path.

23 Claims, 14 Drawing Sheets

SENSING ARRANGEMENT FOR CONTROL OF POWERED CUTTING DEVICE

CROSS-REFERENCE TO RELATED APPLICATION

This application claims the benefit of U.S. Provisional Application No. 61/196,957, filed Oct. 22, 2008, the disclosure of which is incorporated herein by reference in its entirety.

FIELD OF THE INVENTION

This invention relates generally to powered surgical handpieces provided with a cutting element thorough which suction is drawn. More particularly, this invention relates to sensing of suction through the cutting element and handpiece for controlling the speed of the cutting element and for controlling a final position of a stopped cutting element.

BACKGROUND OF THE INVENTION

Powered handpieces that receive and operate surgical instruments are well known in the arthroscopy field. The powered handpieces provide a mechanical drive for disposable cutting blades attached thereto. Some cutting blades have a fixed outer tube having a distal opening and an inner cutting tube received therein having a distal opening with cutting teeth. The openings together define an open window when in alignment with each other. A suction arrangement is provided to enable suction of fluid from a surgical site into the inner tube and through the handpiece to a suction device when the openings of the tubes are disposed in alignment with each other to provide a window for a flow path between the exterior of the cutting blade and the suction device.

In operation, the suction arrangement through the handpiece and blade is capable of removing large quantities of fluid from a surgical site within a short period of time. Thus, if the suction window of the cutting blade is in an open position when the cutting blade is stopped, the suction arrangement may rapidly remove fluid from the surgical site resulting in a lower pressure than that required to perform a procedure. If each and every time the handpiece is stopped the inner cutting tube stops with the window formed by the openings in a closed position, fluid management would be improved.

U.S. Pat. No. 5,733,298 to Berman, et al. discloses an endoscopic shaver blade window positioning system for a handpiece that receives an elongate shaver blade assembly. The blade assembly has a movable inner elongate member having a cutting opening at its distal end and a position indicator mounted to a movable hub at a proximal end of the inner elongate member. The position indicator rotates with the inner elongate member. The inner member is received within an elongate outer member having a distal opening. A sensor is fixed on an interior of the handpiece at the distal end thereof. In operation, the sensor detects passing of the position indicator thereby as the movable hub rotates. A window positioning system determines the position of the indicator and thus the blade assembly by determining the position of the indicator with respect to the sensor. The indicator can be a magnet, ferrous metal, bar code, reflective stripe or electrical contact that is detected by the sensor. A window control circuit controls the motor of the handpiece to stop the inner member at a predetermined position relative to the outer elongate member.

U.S. Pat. No. 5,602,449 to Krause, et al. discloses a motor controlled surgical system and method having positional control. The system includes sensors in a motor for generating electrical signals indicating a motor drive position relative to a motor drive initial position. Further, a position identifier for identifying a start-stop position of a driven surgical device is provided so that the surgical device can be stopped at a predetermined position. In other arrangements, an element secured to a rotating portion of a driven member of the surgical device has its position sensed by a sensor element secured to the handpiece that provides an electrical signal to identify when the surgical device is at a predetermined position. Thus, the surgical device may be controlled so that it always starts, ends, and/or reverses, at a known position at which an aperture at a distal end of the surgical device has a predetermined known open, closed, or partially open characteristic.

The above arrangements rely on a sensor and at least one indicator or detectable element provided with the surgical device. Disposing sensors or indicators inside of, or on disposable cutting blades or the like, as disclosed in the above patents can be of concern. Specifically, such an arrangement increases the overall cost of disposable cutting blades. Further, the cutting blades can only be utilized with a handpiece having the appropriate sensor/device for determining the position thereof.

The invention in one embodiment provides a sensor inside the shaver handpiece for detecting the position of a disposable cutting accessory so that the cutting accessory does not require a sensor or an indicator mounted thereon, while maintaining the ability to provide a selected open, partially open, or closed window for the cutting accessory of the handpiece when the accessory is stopped. Another embodiment disposes the sensor away from both the cutting accessory and the handpiece. Another embodiment enables a determination of the relative operating speed of an inner cutting element of a cutting accessory. Other embodiments optimize the cut/bite of the cutting accessory by controlling the cutting speed of the inner cutting element. Finally, another embodiment detects clogging of a suction path of the cutting accessory.

In another embodiment, the invention utilizes a pressure sensor to monitor pressure in a suction path for a handpiece having a cutting accessory attached thereto. The cutting accessory is defined by a movable cutting element and a fixed cutting element having openings or apertures at distal ends thereof. A window is defined by the movable and fixed cutting elements. As the movable cutting element rotates or reciprocates, the window closes and opens to periodically define a suction path. A pressure difference occurs in the suction path each time the window opens/closes. Thus, a resulting pressure pattern has minimum and maximum pressure values occurring at a frequency that corresponds to the frequency of rotation or reciprocation of the inner cutting element. When the cutting window defined by a movable cutting element and a fixed cutting element is open, an increase in measured pressure occurs, and when the cutting window is closed, a pressure decrease in the suction tube occurs. Thus, the pressure sensor determines the velocity of movement for the inner cutting element relative to the outer cutting element.

Besides tracking the velocity of the inner cutting element, the pressure sensor can determine the location of the opening of the inner cutting element relative to the opening of the outer cutting element. Measured pressure values enable a control system to track the location of the inner cutting element and to adjust the location of the window to a desired final position when the inner cutting element is stopped. For example, the inner cutting element can be stopped with its opening at a closed position relative to the opening of the outer cutting element. This arrangement enables fluid management for a cutting accessory located at a surgical site.

In one embodiment, a pseudo smart-handpiece is provided with a pressure sensor in the suction flow path of the handpiece. A controller in the handpiece can adjust the speed of rotation of the inner cutting element depending on the pressure sensed by the pressure sensor and measured joint pressure to obtain a predetermined desired average fluid flow rate along the suction path. By adjusting speed of the inner cutting element due to suction pressure and joint pressure, the bite/cut of the cutting element can be maximized.

Further, a change of pressure, such as a sudden decrease in pressure may be measured to indicate a clogging of the cutting window. In such instance, the suction pressure would remain low as no fluid is drawn through the window.

In one embodiment a fluid flow sensor is provided in a suction path for a handpiece having a cutting accessory attached thereto as discussed above. As the movable cutting element rotates or reciprocates, the window opens and closes so that a measurable flow difference occurs periodically. Thus a fluid flow pattern results having maximum and minimum flow values occurring at a frequency that corresponds to the frequency of rotation or reciprocation of the inner cutting window.

Besides tracking the velocity of the inner cutting element, the flow sensor determines the location of the opening of the inner cutting element relative to the fixed outer cutting element. Thus, the inner cutting element can be stopped at a desired final position, for instance with the window in a closed position. Further, sensing essentially no fluid flow while the inner cutting element is rotating or reciprocating indicates clogging of the cutting window.

In another embodiment of the invention, a pseudo smart-handpiece is provided with a flow sensor in the suction flow path of the handpiece. A controller can adjust the speed of rotation of the inner cutting element to maintain the fluid flow through the suction flow path at a predetermined average flow rate taken by averaging the high and low fluid flow values or integrating the flow value measured over a time period to obtain a predetermined optimal overall average fluid flow rate for the liquid, and in many instances cut tissue, passing through the suction bore. This flow control arrangement maximizes the bite/cut of the cutting accessory.

Figure 1:
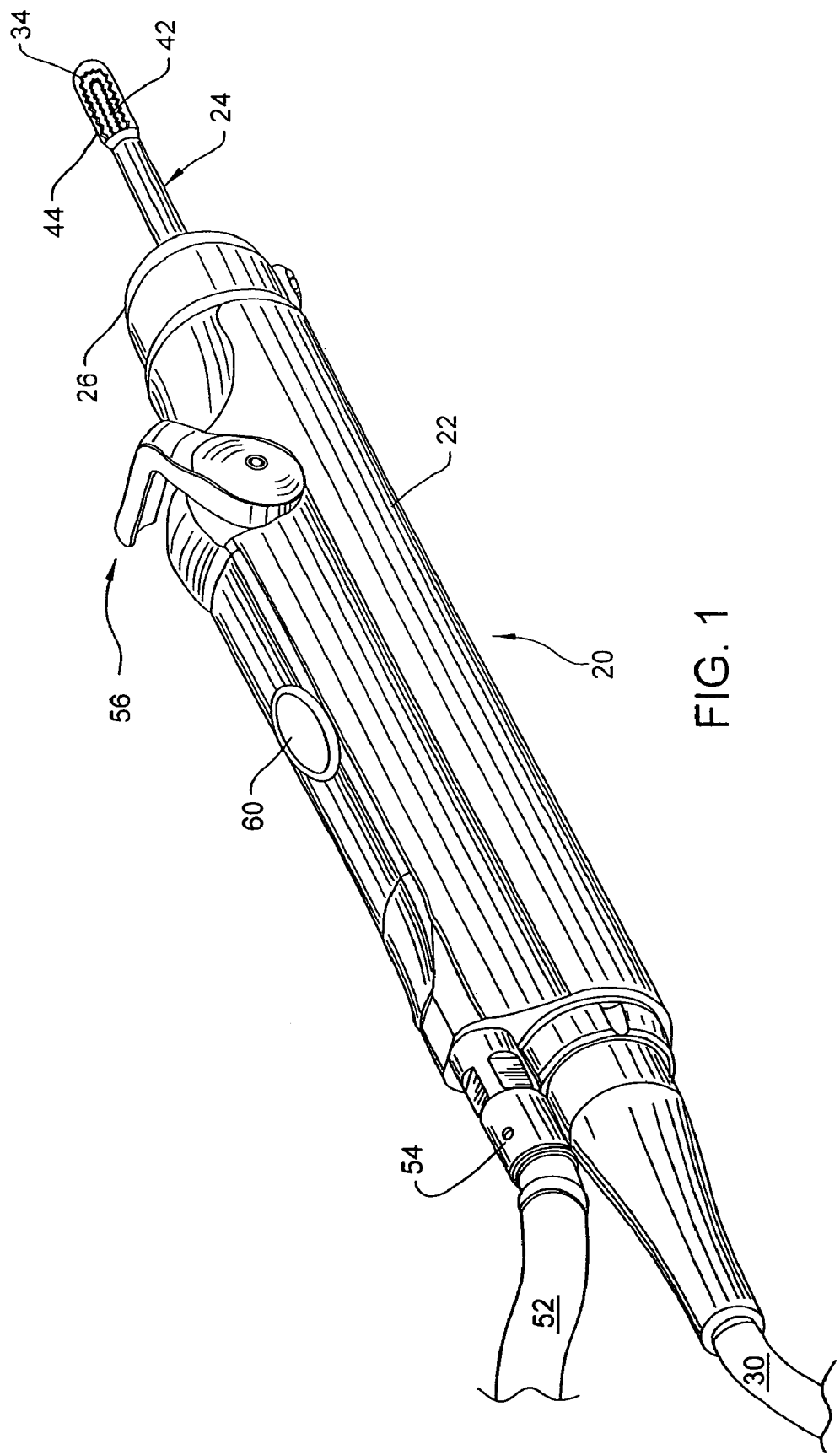
FIG. 1 depicts a perspective view of a powered surgical handpiece with a cutting accessory according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement, and designated parts thereof. Said terminology will include the words specifically mentioned, derivatives thereof, and words of similar import.

DETAILED DESCRIPTION

Figure 2:
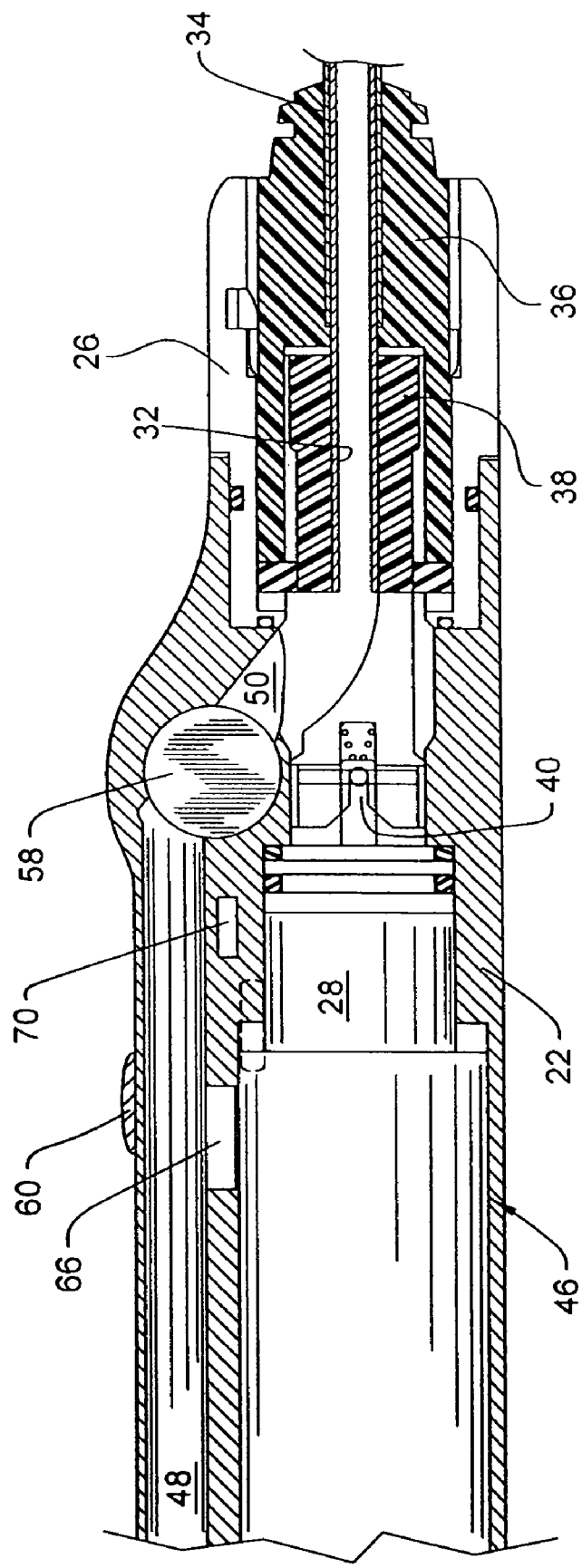
FIG. 2 is a partial cross sectional view of the handpiece and cutting accessory illustrated in FIG. 1.

FIGS. 1 and 2 depict a surgical handpiece 20 of this invention. Handpiece 20 is designed to perform endoscopic surgical procedures, though other embodiments of this invention may be designed to perform other types of surgical procedures. The handpiece 20 includes an elongate housing 22 that functions as the body of the handpiece. A complementary cutting accessory 24 is attached to the front end, also known as the distal end, of the handpiece 20. A coupling assembly 26 that is attached to the distal end of the housing 22 releasably couples the cutting accessory 24 to the handpiece 20. A motor 28 shown in FIG. 2 is disposed inside of the housing 22. Power is supplied to the motor from a power supply (not illustrated) through a power cable 30 attached to the proximal end of the housing 22.

As shown in FIGS. 1 and 2, the cutting accessory 24 includes elongated hollow inner and outer cutting elements 32, 34, such as cutting tubes, respectively. A static hub 36 is attached to the proximal, rear end of the outer cutting element 34. The static hub 36 is held to the handpiece 20 by the coupling assembly 26 so as to hold the cutting accessory 24 to the handpiece. An inner hub 38 is fixed to the proximal end of the inner cutting element 32. The inner hub 38 extends through the coupling assembly 26 and into the open distal end of the housing 22. Inner hub 38 engages a drive shaft 40 that extends out from the forward end of motor 28. Thus, actuating motor 28 rotates the inner cutting element 32 relative to the outer stationary cutting element 34.

Exemplary handpieces that can be modified for use in this invention are disclosed in U.S. Pat. No. 7,682,333 entitled POWERED SURGICAL HANDPIECE WITH PRECISION SUCTION CONTROL, which is hereby incorporated by reference. It should be understood that the above is only one of many handpieces that can be modified for use with this invention.

The distal end of outer cutter element 34 is provided with an opening or window 44 disposed radially from a central longitudinal axis of the elongate hollow outer cutting element 34. Opening 44 is the opening through which a distal opening 42 of inner cutting element 32 is exposed to the environment. The opening 42 at the distal end of inner cutting element 32 is oriented radially from a central longitudinal axis of the inner element. The portions of the outer and inner elements 32, 34 that define openings 42, 44, respectively, have sharp teeth as shown in FIG. 1. In the depicted cutting accessory 24, these teeth perform cutting at a window defined by the openings 42, 44 when they are in alignment. Fluid and debris from the surgical site to which the cutting accessory 24 is applied, flows through openings 42 and 44 when the openings are in radial alignment to provide a flow path into the hollow center of inner cutting element 32.

As shown in FIG. 2, the handpiece housing 22 is formed to have a large diameter main bore 46. The main bore 46 is the space at the distal end of the housing 22 in which the inner hub 38 is seated. Main bore 46 also serves as the space within housing 22 in which the motor 28 and drive shaft 40 are located. Extending parallel with and located above main bore 46 in FIG. 2, the housing 22 is formed to have a suction bore 48 of a smaller diameter than the main bore. A diagonally extending suction passage 50 formed in the distal end of housing 22 provides a fluid communication path from the distal end of suction bore 48 with the distal end of the cutting accessory 24. Suction passage 50 opens at the proximal end of the cutting accessory 24. Suction bore 48 is the bore through which suction is drawn so fluid at a surgical site may pass through aligned cutting element openings 42, 44, through hollow inner cutting element 32 and through suction passage 50. Suction is drawn from the handpiece 20 by a suction pump (not illustrated), that connects to the suction bore 48 of the handpiece 20 through a suction tube 52. More particularly, suction tube 52 is removably attached to a suction fitting 54 that is rotatably mounted at the proximal end of housing 22.

A suction control valve 56 may regulate flow between suction bore 48 and suction passage 50. More particularly, valve 56 is rotatably mounted in a circular valve chamber 58 formed in the housing 22. In FIG. 2, valve chamber 58 connects suction passage 50 to suction bore 48. This suction valve structure is disclosed in commonly owned U.S. Pat. No. 7,682,333 which is incorporated by reference herein.

Figure 3:
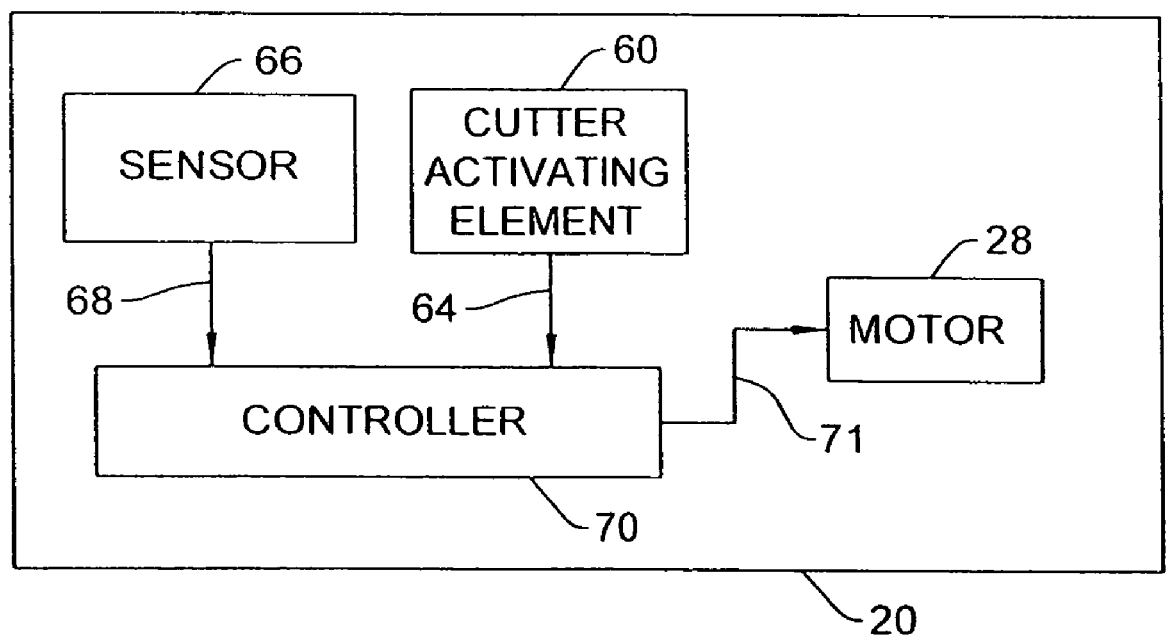
FIG. 3 is a block diagram of elements within the handpiece.

FIG. 1 shows a cutter activating element or switch 60 for providing a cutter control output 64 as shown in FIG. 3 to power the cutting accessory 24.

As shown in FIG. 3, sensor 66 senses pressure or fluid flow in the suction bore 48 and provides a flow rate or pressure output 68. The controller 70 disposed in the handpiece 20 receives cutter control output 64 and sensor output 68 as inputs thereto. As shown in FIG. 3, controller 70 provides a controller output 71 to control the motor 28.

Pressure Measurement and Control Embodiments

Figure 4:
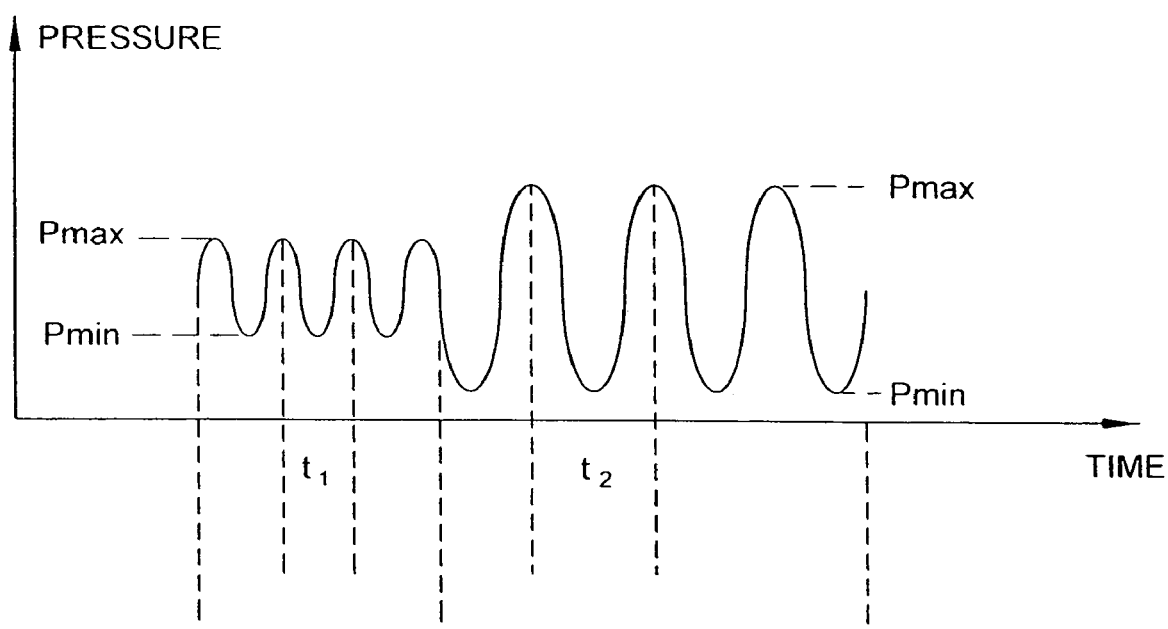
FIG. 4 is a waveform illustrating sensed pressure within a suction flow path of the handpiece.

In a first embodiment, the sensor 66 is a pressure sensor that provides a pressure sensor output 68. The pressure output 68 has maximum pressure values $P_{max}$ and minimum pressure values $P_{min}$ as shown in the waveform of FIG. 4. The pressure values change due to the opening and closing of the window during rotation of inner cutting element 32. Each time openings 42 and 44 are in alignment, the suction pressure is at a maximum pressure value $P_{max}$ at the peak of the waveform as shown in FIG. 4. When the window is closed, a minimal valley pressure $P_{min}$ results. The inverse of time periods $t_1$ and $t_2$ in FIG. 4 define respective frequencies $f_1$, $f_2$ that correspond to the velocity or speed of inner cutting element 32.

Operation

In operation, a user operates the cutter activating element 60 shown in FIG. 1 to power the cutting accessory 24. The controller 70 receives the cutter control output 64 and the pressure sensor output 68 from pressure sensor 66. The controller 70 then operates the cutting accessory 24 in accordance with the flow charts illustrated in FIGS. 5-9 and as discussed below.

Figure 5:
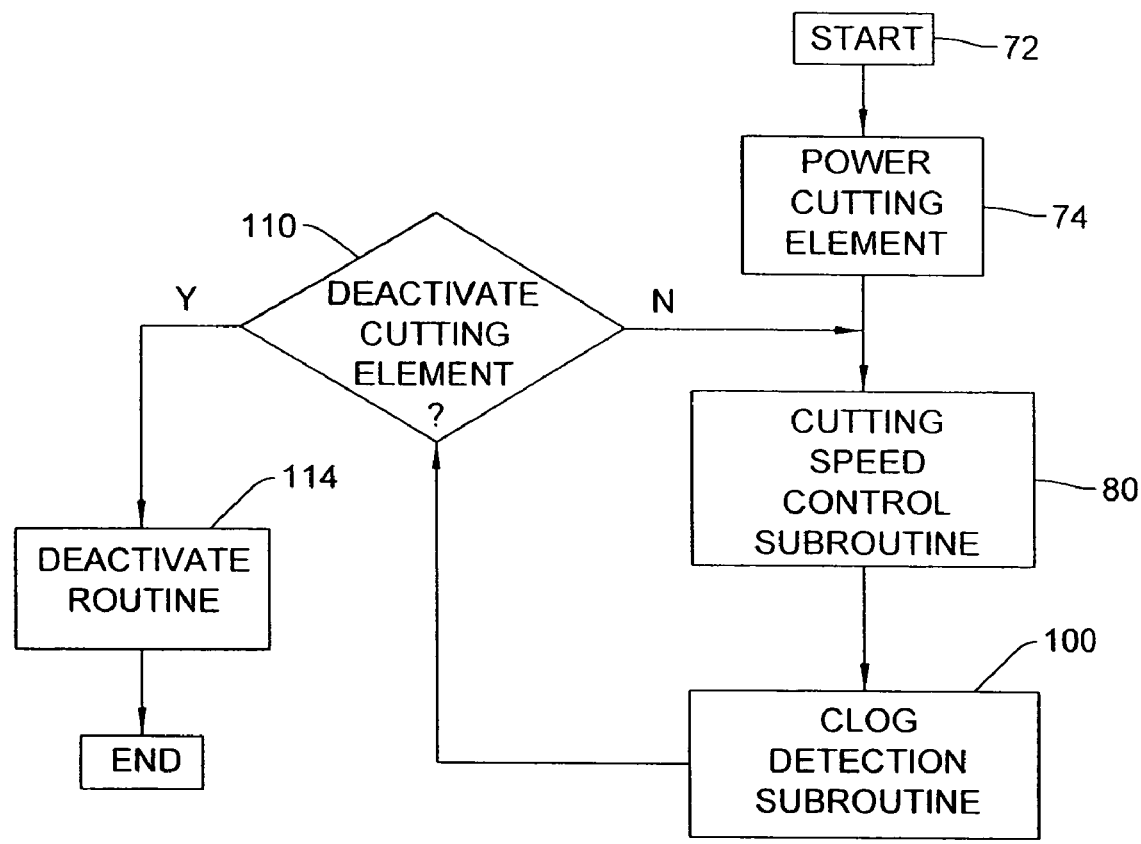
FIG. 5 is a flow chart illustrating operation of the powered handpiece.

The flowchart of FIG. 5 illustrates operation of the controller 70 including start step 72 when cutter activating element 60 is enabled. At step 74, the controller 70 receives cutter control output 64 and starts rotating or reciprocating inner cutter element 32 by controlling power to motor 28. The controller 70 then advances to optimizing subroutine 80 for controlling the speed of the inner cutting element 32 to obtain the most optimal, efficient cut speed or bite speed for the cutting accessory 24, while providing an appropriate pressure within a surgical site, such as a joint, whereat the distal end of the cutting accessory is located.

Cutting Speed Control

Fluid flow optimization is obtained by changing the cutting speed of the inner cutting element 32 in response to changes in pressure in the suction bore 48. Providing or maintaining a predetermined constant average fluid flow rate for liquid and tissue passing through the suction bore 48 results in an improved or maximized cut/bite during operation of the cutting accessory 24.

Figure 6:
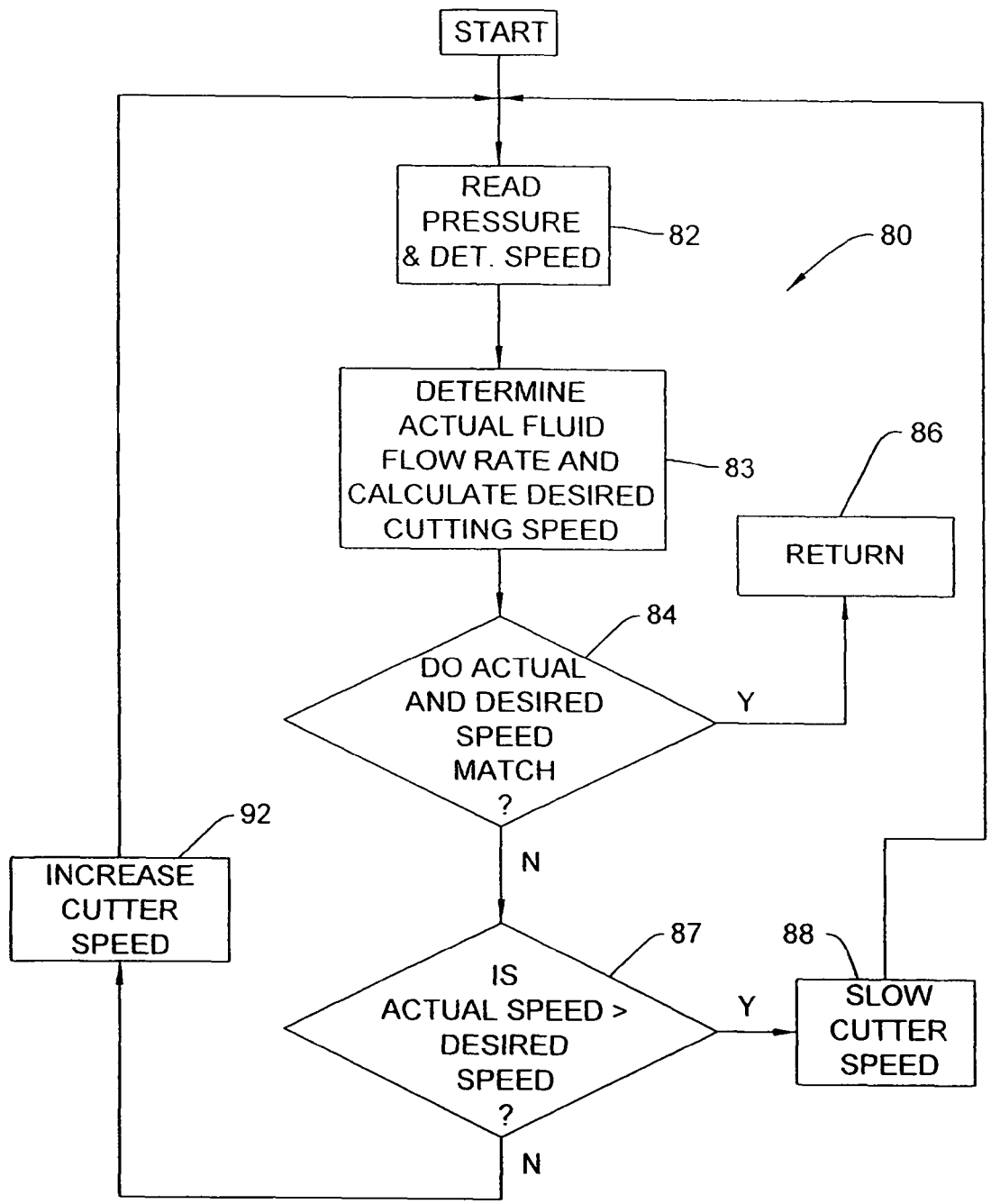
FIG. 6 is a flow chart illustrating a subroutine for control of cutter speed.

Cutting speed control subroutine 80 is represented by the flow chart shown in FIG. 6. The subroutine 80 includes step 82 whereat controller 70 receives pressure sensor output 68 and determines minimum and maximum pressure values $P_{min}$, $P_{max}$ for the measured pressure from pressure sensor 66 disposed within the suction bore 48. Further, the frequency, for example $f_1$ or $f_2$, is calculated from the inverse of the time periods $t_1$, $t_2$ defined by minimum and maximum pressure values $P_{min}$, $P_{max}$ shown in FIG. 4 to determine an actual speed or velocity for the inner cutting element 32.

At obtaining desired speed step 83, an optimal cutting speed for the inner cutting element 32 is calculated. Additional pressure values corresponding to underlying joint pressure at the surgical site are provided, and the pressure difference between the measured joint pressure and the suction bore pressure result in a pressure differential so that an actual average fluid flow rate value is calculated. The average actual fluid flow rate through the suction bore 48 of the handpiece 20 is compared to an optimal average fluid flow rate to obtain a desired new cutting speed that will result in the predetermined optimal average fluid flow rate.

At step 84, the controller 70 determines if the measured actual cutting speed of the inner cutting element 32 matches the desired cutting speed. If the speeds match, the optimizing subroutine 80 ends and the controller 70, at step 86, returns to the flow chart illustrated in FIG. 5. If, however, the actual cutting speed is not the desired optimal speed correlated from the measured pressure value, the controller 70 advances to step 87.

At step 87, the controller 70 determines if the measured actual cutting speed is greater than the desired calculated cutting speed. If yes, the controller 70 advances to step 88. At step 88, the controller 70 controls the motor 28 to decrease the actual cutting speed. After slowing the actual cutting speed, the controller 70 returns to step 82 to read new pressure values including $P_{min}$, $P_{max}$ with the pressure sensor 66, again determines actual cutting speed of the inner cutting element 32. The controller 70 then advances to step 83 to calculate an average fluid flow rate for fluid through the suction bore 48. This value is correlated with a desired optimal fluid flow rate and the actual cutting speed to obtain a new desired cutting speed that will result in an optimal fluid flow rate.

At step 84, if the actual speed equals the new optimal cutting speed for the inner cutting element 32, the subroutine ends at step 86. If not, the controller 70 again advances to decision step 87. If the measured speed is again too fast, the controller 70 advances to slowing step 88 to slow the cutting element 32. The controller 70 then returns to step 82 and repeats the pressure measuring and advances to step 84 to determine a new optimal cutting speed.

In another instance, when the actual speed measured or calculated at step 82 is determined to be different than a desired speed at step 84, the controller 70 advances to step 87 wherein the actual cutting speed is determined to be slower than the optimal cutting speed. In this instance, the controller 70 advances to step 92 and increases the cutting speed of cutting element 32. Thereafter, the controller 70 returns to step 82 for reading the pressure and determining actual speed. Then at step 83, the controller again determines a desired cutting speed. The controller advances to step 84 and if the actual speed is again less than a desired speed, the controller 70 repeats steps 87, 92, 82, 83, 84 until the actual speed equals the desired cutting speed at step 84. Then the subroutine ends at step 86 and the controller 70 returns to the flowchart of FIG. 5.

In some embodiments, if the cutting speed is not at the desired speed at step 84, after the controller 70 repeats steps 87, 88, 82, 83, 84 or steps 87, 92, 82, 83, 84 a predetermined number of times without the actual cutting speed equaling the desired cutting speed, the controller exits the subroutine 80 and returns to the flow chart shown in FIG. 5.

Clog Detection

Figure 7:
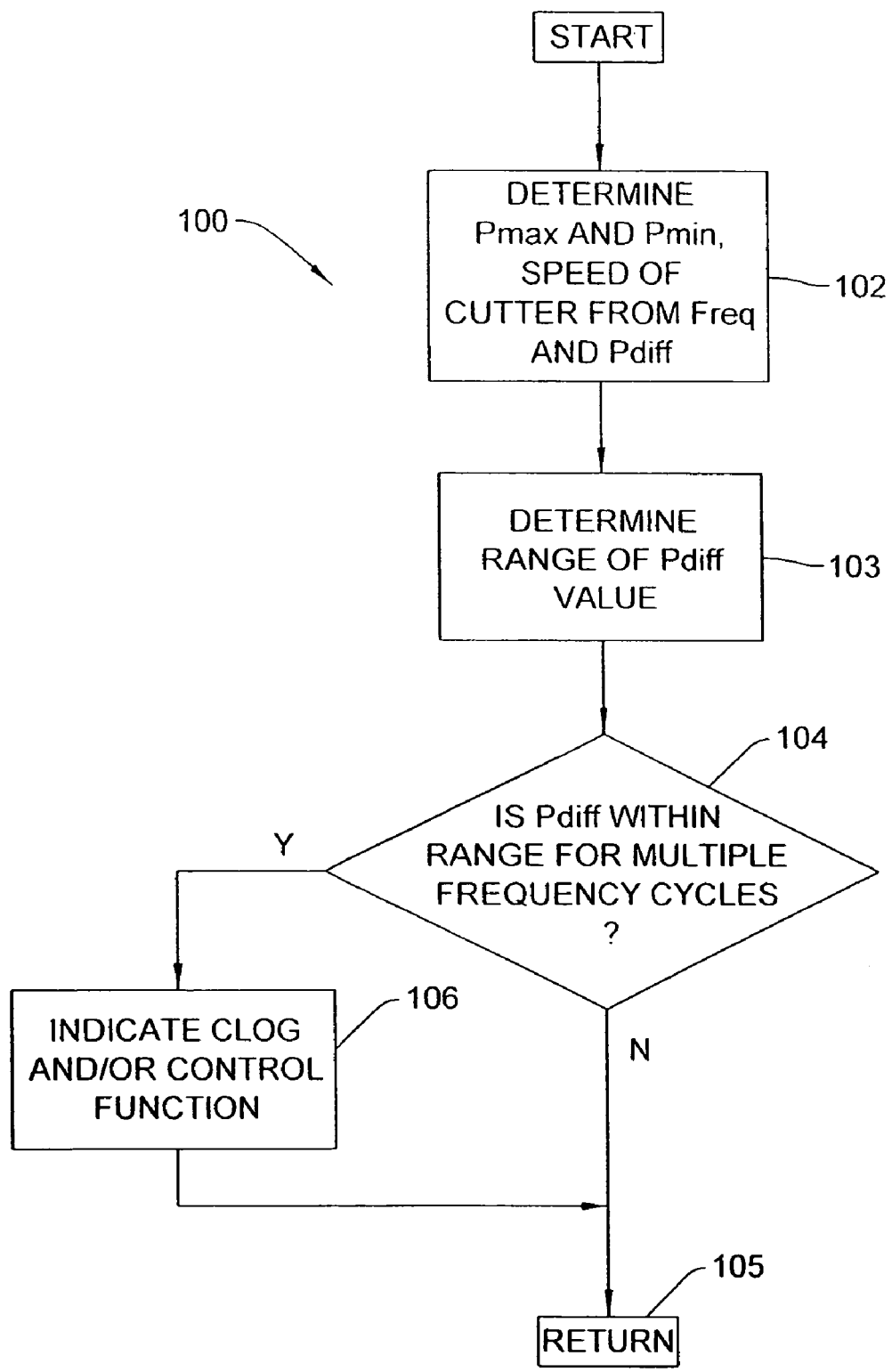
FIG. 7 is a flow chart illustrating a subroutine for the detection of a clog in the suction flow path.

As shown in the flow chart of FIG. 5, after controlling the speed of the cutting element 32, the controller 70 then advances to clog detecting subroutine 100. As illustrated in FIG. 7, at measuring and determining step 102 the pressure sensor 66 senses pressure values, including maximum and minimum pressure values $P_{max}$, $P_{min}$ and determines a frequency from the pressure values, which provides the actual speed of the inner cutting element 32. The controller 70 also compares the pressure values to calculate the pressure drop between $P_{max}$ and $P_{min}$, to obtain pressure difference values for at least two cycles.

At step 103, the pressure difference values are compared with stored values defining a clogged condition range of pressure difference values. The lower and upper condition range values are modified according to the actual speed of the inner cutting element 32 to more accurately determine the presence of a clog. Joint pressure at a surgical site is not measured or a necessary factor in clog detection.

At step 104, if the pressure difference values are outside the clogged condition range and the motor 28 is operating, the controller 70 exits from the clog detecting subroutine 100 and at return 105 returns to step 110 in the flow chart of FIG. 5.

If the pressure differences are within the clogged condition range for at least two consecutive frequency cycles, clogging is detected and the controller 70 advances to step 106 to provide an indication of a clog in the suction flow path. At step 106, an indication can be provided visually or audibly to an operator. After step 106, the controller 70 then exits subroutine 100 and returns to the flowchart as shown in FIG. 5.

In some embodiments, an automatic clog control flush device attempts to unclog the flow path by providing a back flush of fluid to the cutting accessory 24. In these embodiments, the subroutine 100 then repeats to determine if the clog was removed.

FIG. 5 shows controller 70 advancing to deactivation step 110. At deactivation step 110, the controller 70 determines if cutter activating element 60 is actuated. If so, the controller 70 returns to optimizing step 80 and the entire control arrangement continues to operate.

Figure 8:
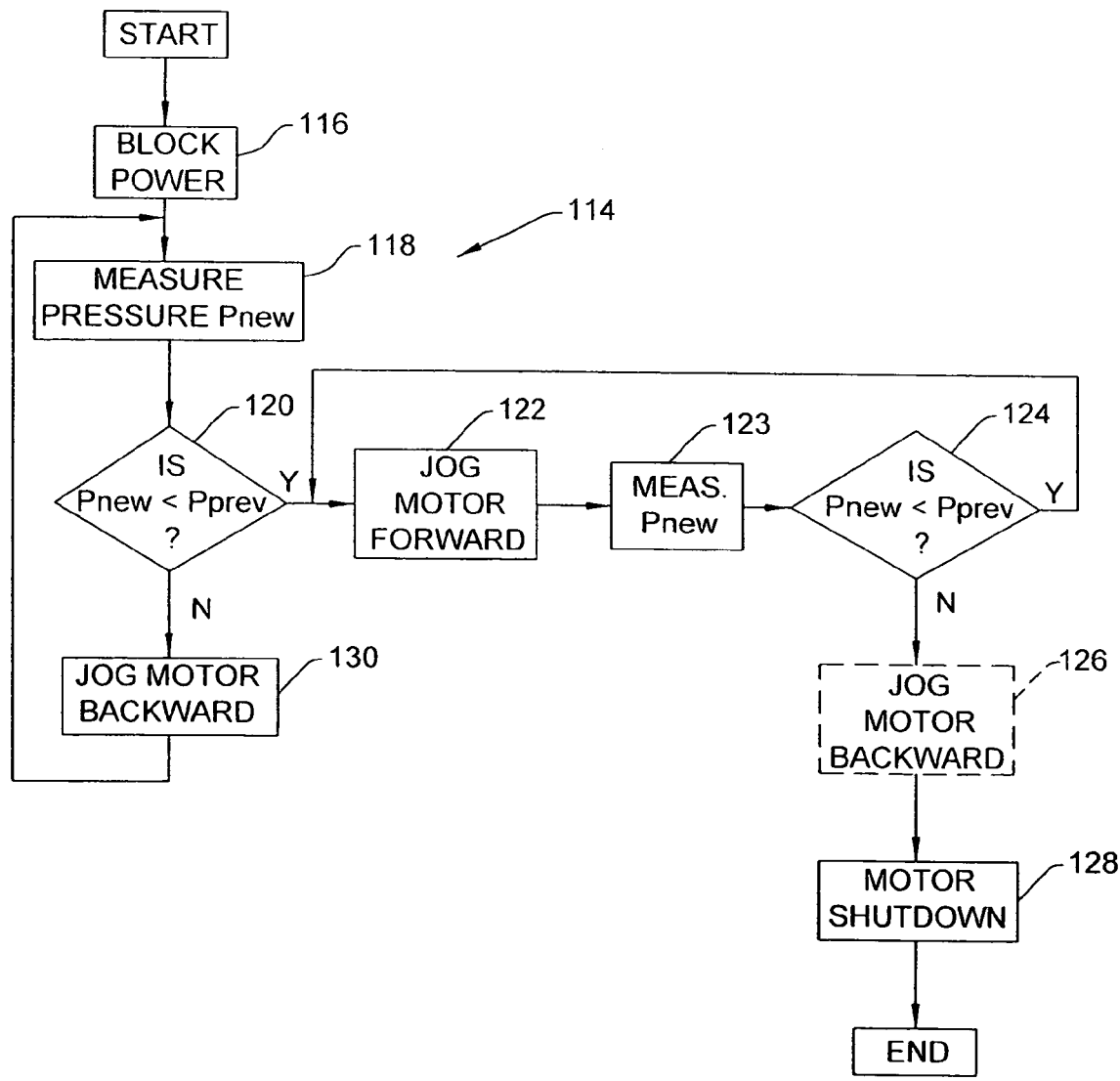
FIG. 8 is a flow chart illustrating a subroutine for placing an opening of an inner cutting element in a closed position relative to an opening of an outer element.

At step 110, however, if the cutter activating element 60 is deactivated or released, the controller 70 advances to cutter stop subroutine 114 illustrated in FIG. 8. Further, throughout the subroutines and the flow chart of FIG. 5, if the actuator 60 is released, the controller 70 advances to subroutine 114.

Cutter Stop Closed Position Subroutine

In subroutine 114 shown in FIG. 8, at power blocking step 116, the controller 70 begins blocking power to the motor 28 in order to stop the cutting accessory.

At step 118, the controller 70 measures pressure values P, with the pressure sensor 66. At step 120, the latest measured pressure value $P_{new}$ is compared with the previously measured pressure value $P_{prev}$. If the new pressure value $P_{new}$, is less than the previous pressure value $P_{prev}$, the controller 70 advances to step 122 and motor 20 is jogged forward. The pressure P is then measured again at step 123 and $P_{new}$ is compared at step 124 with the previously measured pressure value $P_{new}$, which now becomes $P_{prev}$. If the newly measured pressure $P_{new}$ is less than the previously measured pressure $P_{prev}$ at step 124, the controller 70 returns to step 122 and jogs the motor 28 forward again. At step 123, the pressure is again measured and at step 124, $P_{new}$ is compared with the previous pressure $P_{prev}$. If the latest pressure $P_{new}$ is greater than the previous pressure $P_{new}$ at the comparison step 124, the controller advances to optional motor backward step 126 whereat the motor 28 is jogged backward. Then, the controller 70 advances to step 128, whereat the inner cutting element 32 is at a desired position. At step 128, power to the motor 28 is completely removed and the motor cannot be jogged forward or backward. Thus, the cutting stop subroutine 114 ends as power to the motor 28 is discontinued.

The jogging motor backward step 126 shown in broken line in FIG. 8 is optional. If the window of the inner cutting element 32 is at a closed position, there may be no need to jog the motor 28 backward. As discussed above, at a closed position the pressure in the suction bore 48 is at a low value due to the suction applied thereto by a pump while the cutting window 42, 44 defined by inner cutting element 32 and outer cutting element 34 is in a closed position.

In instances where the pressure $P_{new}$ at step 120 is greater than the previous pressure $P_{prev}$, the motor 28 is jogged backward at step 130. The controller 70 then returns to step 118 to again measure the pressure and determine if the new pressure $P_{new}$ is less than the previous pressure $P_{prev}$. If not, the motor 28 is again jogged backward at step 130. This sequence of steps repeats until $P_{new}$ is greater than $P_{prev}$. Then, the controller 70 advances to step 122 and jogs the motor forward. At step 124, the new pressure $P_{new}$ is again compared to the previous pressure $P_{prev}$. If the new pressure $P_{new}$ is not less than previous pressure $P_{prev}$, the controller 70 advances to optional operational step 126 to jog the motor backward to the peak minimum pressure value and then advances to step 128 to completely shut down power to the motor 28, as discussed above.

Operation of the controller 70, as shown in the FIG. 8 cutter stop subroutine, results in the minimum pressure $P_{min}$ for the pressure sensor 66 when the motor 28 is stopped. In this subroutine, the pressure is measured for each position of the motor 28, so that a $P_{min}$ value is obtained and the motor then is stopped and power discontinued.

In other embodiments, however, the pressure value comparison can be changed with regard to the FIG. 8 flow chart so that a pressure corresponding to a predetermined desired pressure is provided in the suction bore 48 as follows.

Cutter Stop Partially Open Subroutine

Figure 9:
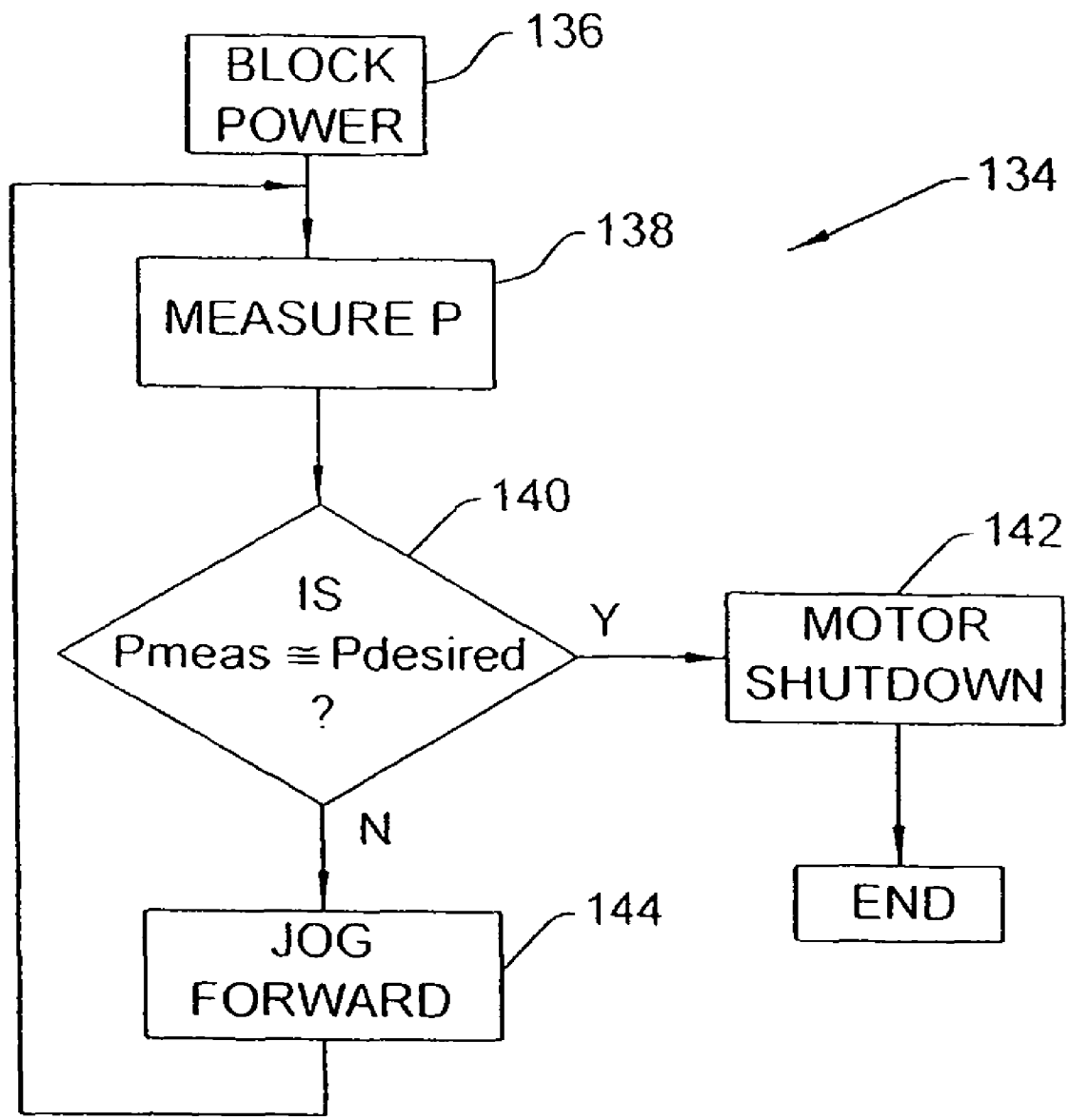
FIG. 9 is a flow chart illustrating a subroutine for placing an opening of an inner cutting element in a partially open position relative to an opening of an outer element.

As shown in FIG. 5, when step 110 indicates the cutting accessory must be deactivated, the controller advances to a cutter stop closed subroutine 114. In the embodiment of FIG. 9, the cutter stop partially open subroutine 134 replaces the subroutine 114.

As in subroutine 114, at first step 136, operation of the motor 28 begins being blocked. At step 138, the pressure sensor 66 measures a pressure value $P_{meas}$. At step 140, the value $P_{meas}$ is compared with a desired pressure value $P_{desired}$ that corresponds to a predetermined window position of the opening 42 of the movable inner cutting element 32 relative to the stationary opening 44 of the outer cutting element 34.

If $P_{meas}$ approximately equals $P_{desired}$ at step 140, the controller 70 advances to step 142. At step 142, the motor 28 is shut down completely and the controller 70 and the motor are completely stopped. The routine shown in FIG. 9 then ends.

If $P_{meas}$ does not equal $P_{desired}$, the controller 70 advances to step 144. At step 144, the controller jogs the motor 28 forward to change the position of the opening 42 relative to opening 44. The pressure is again measured at step 138.

At step 140, $P_{meas}$ is again compared to $P_{desired}$. If the values are not approximately equal, steps 144, 138 repeat.

In this way, a predetermined desired suction pressure value is provided by partial opening of the window defined by the openings of cutting elements 32, 34 of the cutting accessory 24. In some embodiments, the pressure value may correspond to a flow rate value for fluid flow through the suction bore 48.

The above FIG. 9 embodiment is intended for a rotating inner cutting element 32 or a reciprocating cutting element.

Further, the flow chart arrangement in FIGS. 5-9 show exemplary embodiments of the invention. Other flow chart arrangements providing essentially the same results with different steps are also contemplated.

Throughout the pressure sensing embodiments, $P_{max}$ corresponds to maximum pressure sensed by pressure sensor 66 due to maximum flow passing through the suction bore 48. $P_{min}$ corresponds to minimum pressure whereat essentially no flow is provided through the suction bore 48 and thus the pressure value is lower due to suction from the suction pump while the cutting element 32 of the cutting window 42, 44 is in a closed position.

Flow Measurement and Control Embodiments

The fluid flow measuring sensor embodiments are also structurally shown by the arrangement illustrated in FIGS. 1-3. In these embodiments, the sensor 66 comprises a flow sensor 66 providing a flow rate output 68, instead of a pressure output.

Figure 10:
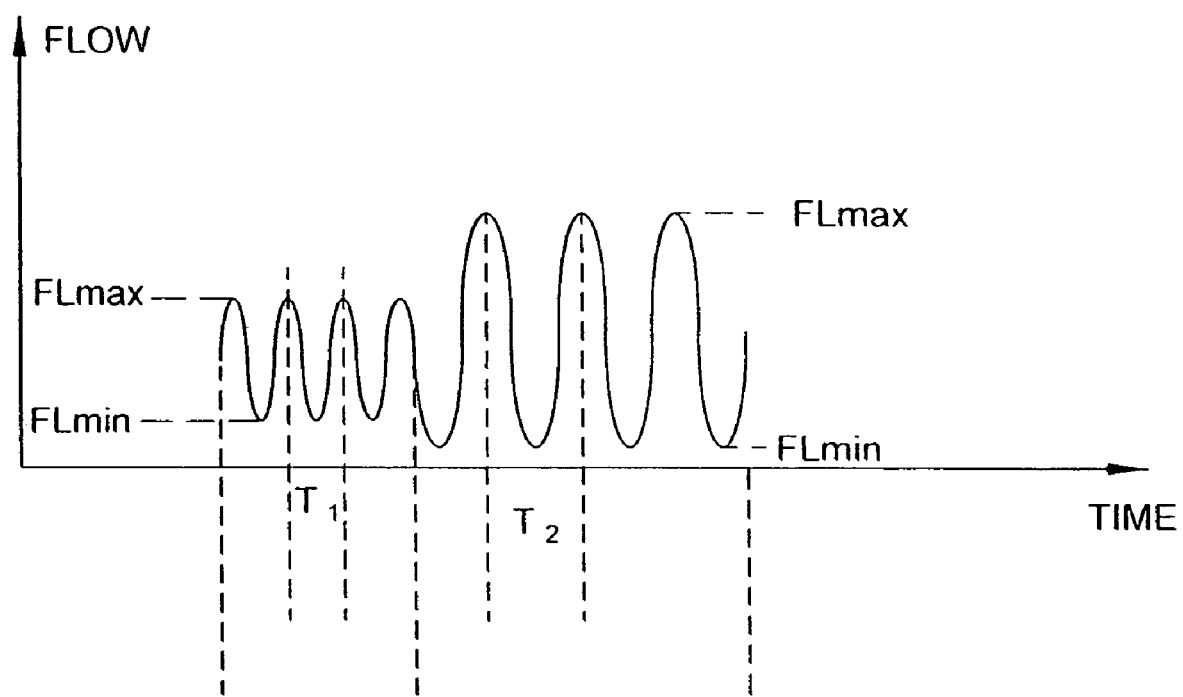
FIG. 10 is a waveform illustrating sensed fluid flow within a suction flow path of the handpiece.

The flow sensor 66 measures maximum flow values $FL_{max}$ and minimum flow values $FL_{min}$ as shown in FIG. 10. The flow values change due to the opening and closing of the window during rotation of inner cutting element 32. Each time the openings 42, 44 are in alignment, a maximum flow value $FL_{max}$ is sensed as shown in FIG. 10. When the window is closed, a minimal flow rate is measured by flow sensor 66.

FIG. 10 shows time periods $T_1$, $T_2$ corresponding to two different velocities for the inner cutting element 32. Frequencies $f_1$, $f_2$ for the time periods $T_1$, $T_2$ are calculated by inverse values of each of the time periods $T_1$, $T_2$.

The fluid flow rate of the suction fluid, including liquid and tissue passing through the suction bore 48, is sensed by any one of a plurality of different types of sensors. In one embodiment, the flow sensor 66 comprises an ultrasonic flow sensor provided with a transducer. An ultrasonic wave is emitted by the transducer and received by the same or by additional different transducers. In some embodiments, the transducers are piezoelectric transducers. In some embodiments, the flow rate can be calculated by the time of transit of the ultrasonic waves. In another embodiment, Doppler Effect is used to determine flow rate. In other embodiments, a magnetic flow meter is provided. Optical flow sensors and other known sensing arrangements are also contemplated to determine fluid flow through the suction bore 48.

Operation

In operation, a user operates the activating element 60 to power the cutting accessory 24. The controller receives the cutter control output 64 and the flow sensor output 68 from the flow sensor 66. The controller then operates the cutting accessory 28 as discussed below.

The flowchart of FIG. 5 discussed above with respect to the pressure sensing embodiments of the invention also corresponds to the flow sensor embodiments. The differences of the flow sensing embodiments with regard to the pressure sensing embodiments are provided within the operating subroutines 80/100/110 of the pressure sensing arrangement.

Cutting Speed Control

Optimizing of fluid flow rate in response to flow sensor output 68 is obtained by controlling the speed of the inner cutting element 32 in response to fluid flow rate. In the subroutine 160 of FIG. 11, controller 70 receives the flow sensor output 68 and at step 162 simply determines an average flow rate from the flow output 68 received from the flow sensor 66 over a desired time period.

The measured average flow value $FL_{AVE}$ is compared with a predetermined known optimal average flow rate value at step 164. If the actual measured average flow rate value $FL_{AVE}$ is the same as the optimal desired flow rate at step 164, the subroutine 160 ends at step 166.

If the flow rate value $FL_{AVE}$ is different than the predetermined optimal average flow rate value at decision step 164, the controller advances to decision step 167.

Figure 11:
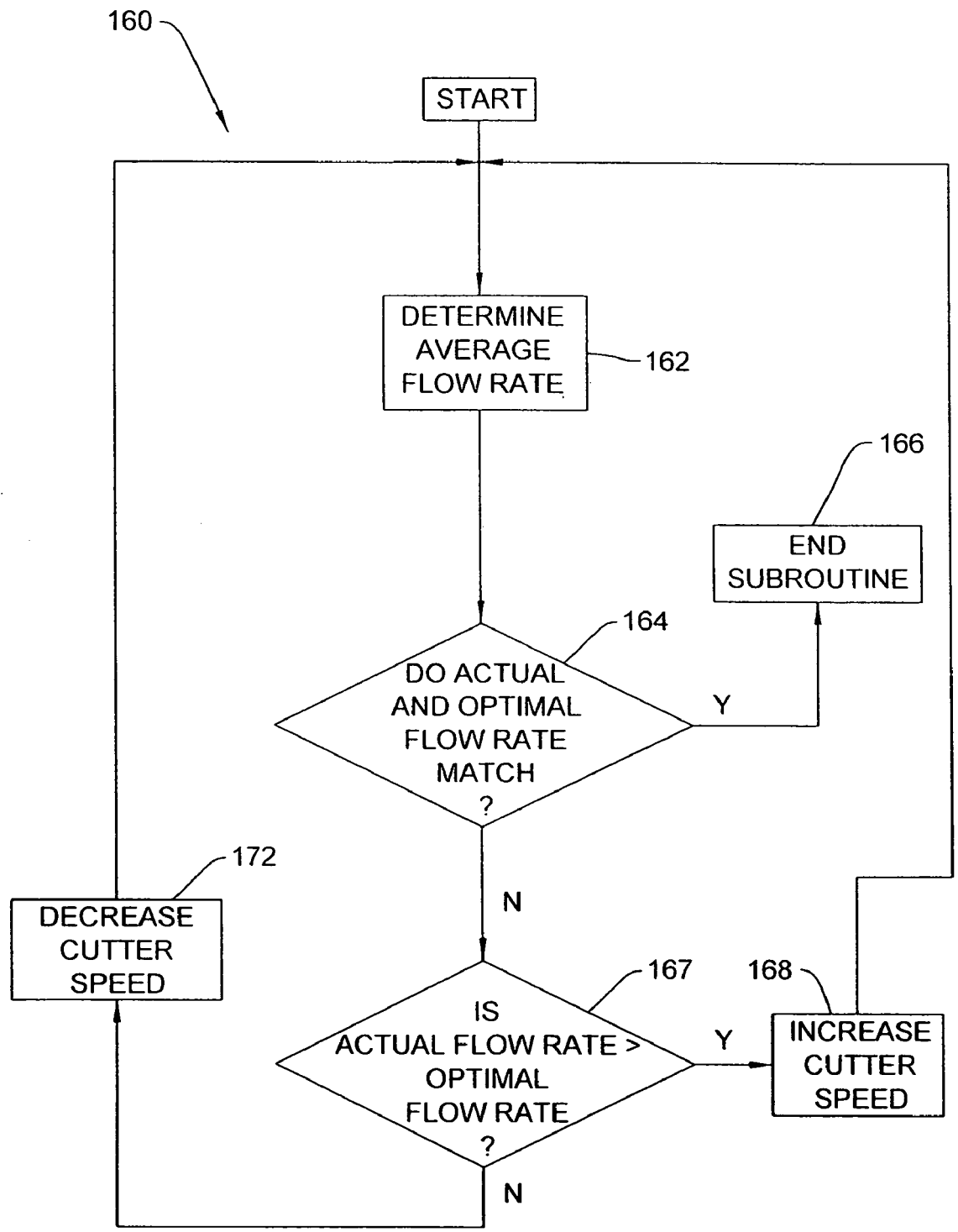
FIG. 11 is a flowchart illustrating a subroutine for operating the cutting accessory at a maximized cut/bite.

At step 167 shown in FIG. 11, if the flow rate value $FL_{AVE}$ is greater than the optimal flow rate value, the controller 70 advances to step 168 and increases the speed of cutting element 32 to decrease the flow rate through the suction bore 48. The controller 70 then returns to step 162 and repeats the subroutine.

At step 167, if the flow rate value $FL_{AVE}$ is less than the optimal flow rate value, the controller 70 advances to step 172. At step 172, the speed of the cutting element 32 is decreased to increase the fluid flow rate.

The controller 170 then advances to step 162 and repeats the subroutine 160 until the flow rate value $FL_{AVE}$ and the optimal flow rate value essentially match one another.

While the FIG. 11 embodiment does not require a desired speed calculation, such an arrangement is available. In one embodiment, the controller 70 determines the cutting speed from the measured time $T_1$, $T_2$ between minimum and maximum flow rate values $FL_{min}$, $FL_{max}$ as shown in FIG. 10. The inverse values of time periods $T_1$, $T_2$ correspond to frequency values $f_1$, $f_2$ which represent the speed or velocity of the inner cutting element 32. This information can be displayed or used for additional purposes, such as clog detection by the processor 70.

With regard to the above flow rate sensing embodiments, if the proper desired cutting speed or fluid flow rate is not obtained after operating the subroutine 160 a predetermined number of times, the subroutine 160 exits and advances to a clog detecting subroutine.

Clog Detection

With regard to the detection of a clog by the flow sensor 66, the controller 70 obtains the flow output 68 and from the values $T_1$, $T_2$, $FL_{min}$, $FL_{max}$ and calculates the cutting speed. If there is little or essentially no fluid flow while the cutting element 32 is operating at a predetermined speed, the controller 70 outputs a signal to indicate that a clog has occurred. Therefore clog detection is easily performed by the controller 70 in the flow sensing arrangement.

Cutter Stop

Cutter stop close and cutter stop partially open subroutines for the flow sensor embodiments generally correspond to the subroutines illustrated in FIGS. 8 and 9 with regard to the pressure sensor embodiments. The main difference, is that in the cutter stop closed position arrangement the controller 70 jogs the motor 28 of the handpiece 20 until the flow sensor 66 senses essentially no flow through the suction bore 48.

With regard to the partially open subroutine shown in FIG. 9, the controller 70 receives flow sensor output 68 and moves the inner cutting element 32 to a position permitting an optimal desired average fluid flow rate through the suction tube 48.

In view of the above discussion, the flow sensing embodiments that control of the cutting element 32 in response to flow sensor outputs 68 generally are simplified in comparison to the pressure sensing embodiments described in FIGS. 5-9.

Additional Alternatives

The specific handpiece 20 illustrated in FIGS. 1 and 2 is merely one representation of the invention. Other handpieces configured for receiving a cutting accessory 24 and a suction bore arrangement may be utilized with the claimed invention. Likewise, the valve arrangement and suction bore arrangement illustrated in the handpiece shown in FIG. 2 may have different orientations and different valve members at different locations.

Figure 12:
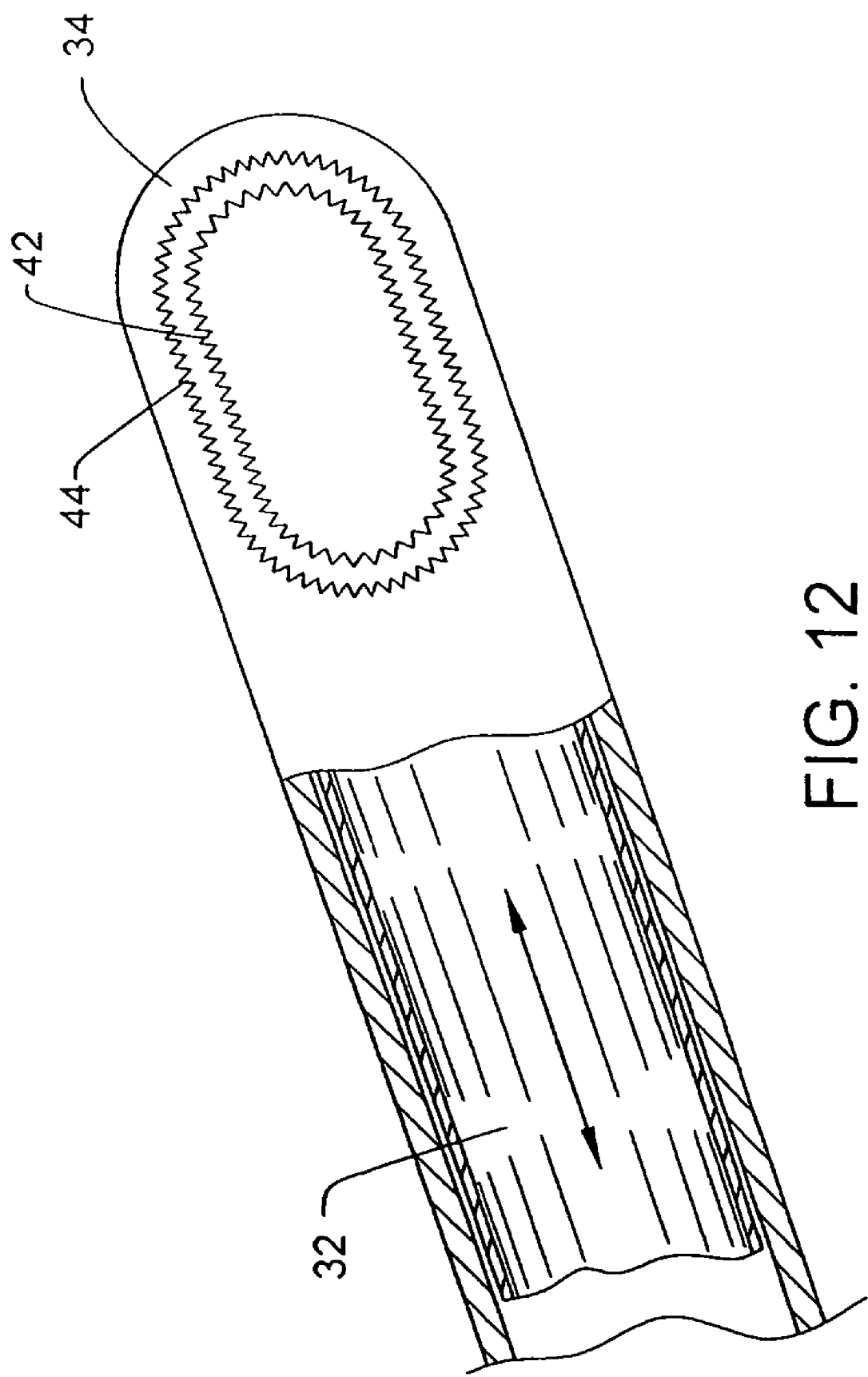
FIG. 12 is an enlarged partial cross-sectional view of the distal end of a cutting accessory.

Further, while FIGS. 1 and 2 show a cutting accessory 24 having a rotating inner cutting element 32, the pressure sensing embodiments and the flow sensing embodiments are also usable with a reciprocating drive arrangement for an inner cutter element 32 of a cutting accessory. As illustrated in FIG. 12, a hollow outer cutting element 34 with an opening 44 for forming a window receives an inner cutting element 32 having an opening 42. The distal end of the reciprocating cutting accessory shown in FIG. 12 appears essentially physically identical to the above described cutting accessory and thus the same reference numerals are provided. The difference from the FIGS. 1 and 2 embodiment is that the inner cutting element 32 is provided with a drive arrangement so that the inner cutting element moves back and forth along the longitudinal axis of the elongate cutting accessory. Thus, in the embodiment of FIG. 12, cutting teeth are provided at least at both circumferentially oriented edges of the respective openings 42, 44.

The subroutines 124, 134 may be modified, if necessary, for the embodiment of FIG. 12 that has the reciprocating inner cutting element 32.

In additional embodiments, the inner cutting element 32 may reciprocate along a path whereat the window defined by openings 42, 44 never completely closes.

In some embodiments, the cutter activating element 60 can be located at any convenient location on the handpiece 20 or may also be mounted away from both the handpiece 22 and the cutting accessory 24.

In some embodiments the cutter activating element 60 may provide a variable speed control signal to the controller. In such embodiments the controller 70 does not calculate a desired speed value. In these embodiments the clog detection and cutting deactivation arrangements may remain.

Additional Sensing Embodiments

Figure 13:
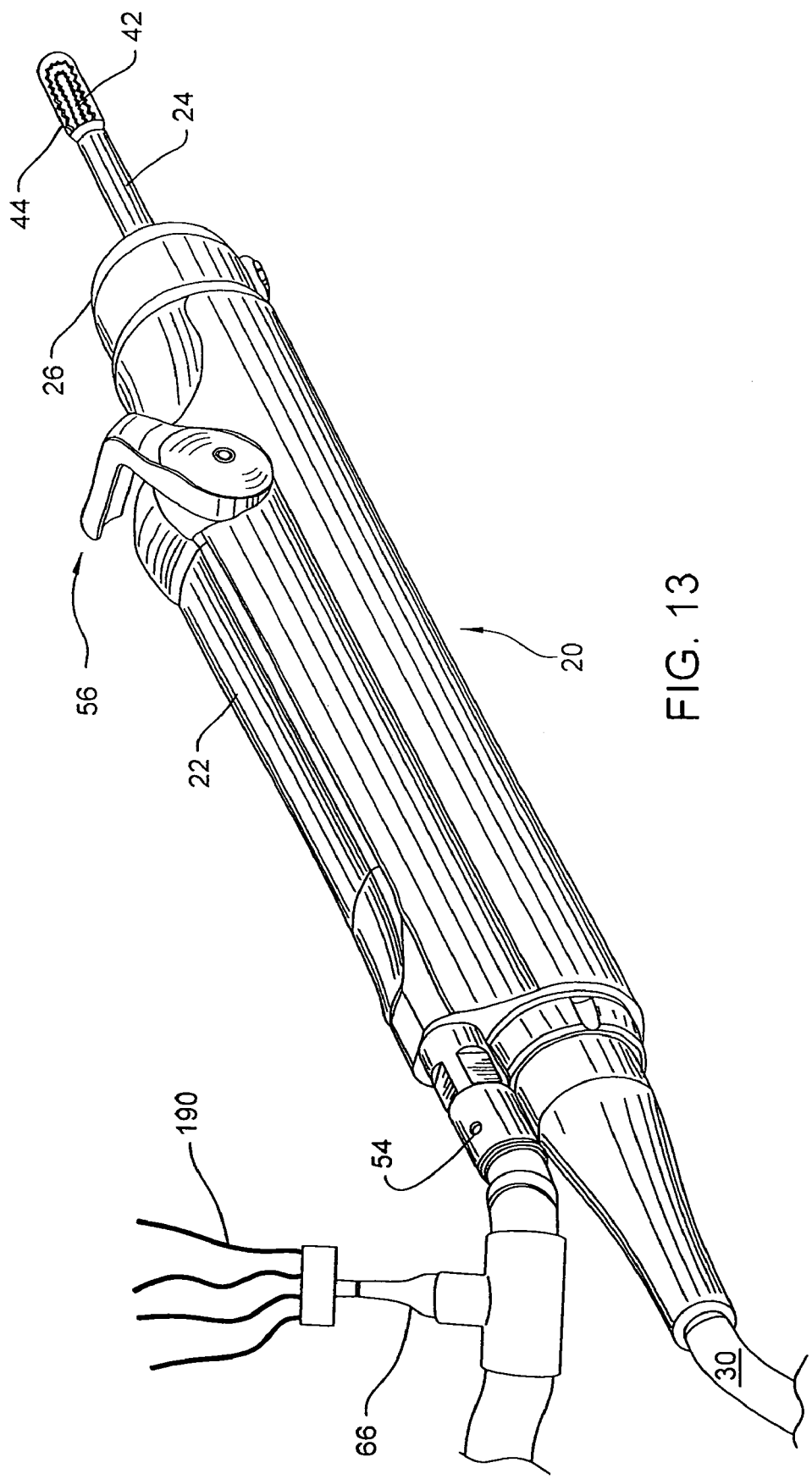
FIG. 13 depicts another embodiment of the invention including a sensor secured to a suction line that is connected to a handpiece.
Figure 14:
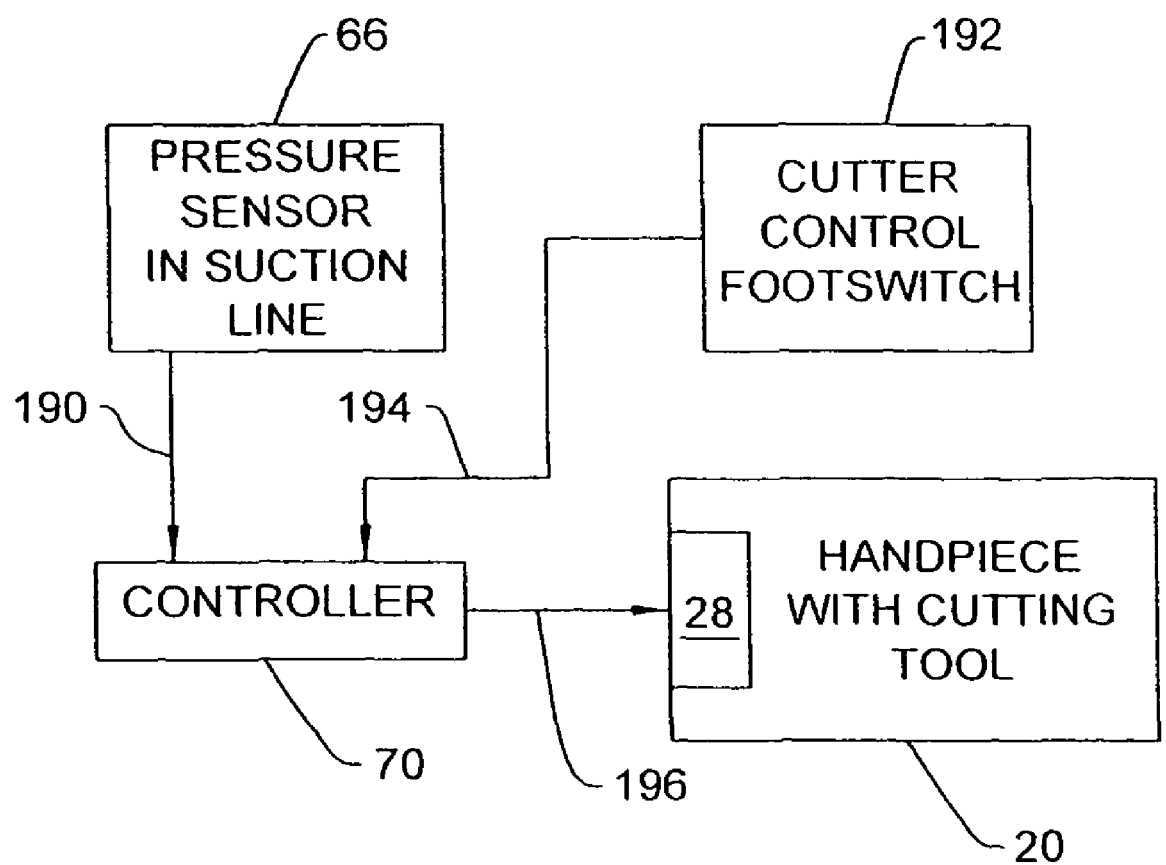
FIG. 14 is a block diagram illustrating a sensing arrangement for control of a cutting accessory attached to a handpiece as illustrated in FIG. 12.

FIGS. 13 and 14 show another embodiment of the invention wherein the sensor 66 is mounted to the suction tube 52 remote from the handpiece 20. The sensor 66 can be a pressure sensor or a flow sensor. In FIGS. 13 and 14, the sensor 66 includes wiring 190 for connection to a controller 70. In the embodiment of FIGS. 13 and 14, a cutter control foot switch 192 outputs an actuation and/or control signal 194 to controller 70. The controller 70 provides a motor control power output 196 to operate the handpiece motor 28.

In one embodiment, the controller 70 is disposed externally of the handpiece 20 and controls power supplied to motor 28 disposed in the handpiece 20 to operate the cutting accessory 24 in an appropriate manner as discussed above.

While a cutter control activating element 60 and a cutter control foot switch 192 are disclosed, other cutter control elements are contemplated, such as various hand control or voice control arrangements.

The motor 28 disclosed herein may be a step motor or other type of motor controllable to jog forward and backward in increments enabling the proper placement of the openings of the inner cutting element 32 with respect to the outer cutting element 34.

Some embodiments of the invention include only one or two of the three subroutines 80, 110, 114/134 and 160 shown in FIGS. 5-9 and 11. Some embodiments with the flow sensor also include only one or two of the three possible subroutines. In some embodiments that do not include a deactivation routine, the inner cutting element 32 stops at a random position when the cutting accessory 24 stops. Other embodiments of the invention do not include clog detection for the cutting accessory 24 and do not include controlling of the speed of the cutting accessory to provide an optimal average fluid flow rate.

Although particular preferred embodiments of the invention are disclosed in detail for illustrative purposes, it will be recognized that variations or modifications of the disclosed apparatus, including the rearrangements of parts, lie within the scope of the present invention.

What is claimed is:

1. A method for operating a handpiece, the method comprising the steps of:
   providing suction through a suction tube to a suction bore in the handpiece, the suction tube and the suction bore comprising a suction path, the handpiece including a coupling assembly at a distal end for coupling to a proximal end of a cutting accessory and the handpiece including a motor for driving the cutting accessory, the cutting accessory comprising a fixed element with an opening at a distal end thereof and a driven element with an opening at a distal end thereof, the openings together defining a window for at least partially opening and closing during movement of the driven element;

actuating the driven element of the cutting accessory by operating the motor;

determining the position of the driven element relative to the fixed element by sensing at least one of pressure and fluid flow in the suction path; and controlling the motor to stop the driven element at a predetermined position in response to the sensed pressure or fluid flow.

2. The method of claim 1, wherein the step of actuating the driven element comprises rotating the driven element within and relative to the fixed element.

3. The method of claim 1, wherein the step of actuating the driven element comprises reciprocating the driven element within the fixed element.

4. The method of claim 1, wherein the sensing step comprises sensing maximum pressure values and minimum pressure values that correspond to a position of the driven element relative to the fixed element, the maximum and minimum values repeating at a frequency corresponding to the velocity of the driven element.

5. The method of claim 4, including the steps of:

comparing the maximum and minimum pressure values over the entirety of at least two time periods to determine when the maximum pressure remains below a predetermined value to detect a clog in the suction path; and informing a user of the presence of a clog.

6. The method of claim 1, wherein the step of stopping the driven element at a predetermined position comprises stopping the driven element at a position relative to the fixed element so that the window defined by the fixed element and the driven element is closed and no fluid is capable of passing from a surgical site through the cutting accessory and into the suction bore of the handpiece.

7. The method of claim 1, wherein the step of controlling the motor to stop the driven element at a predetermined position in response to the sensed pressure or fluid flow comprises stopping the driven element at the predetermined position whereat the opening of the driven element together with the opening of the fixed element define a partial opening.

8. The method of claim 1, wherein the step of determining the position of the driven element relative to the fixed element by sensing at least one of pressure and fluid flow in the suction path comprises sensing at least one of pressure and fluid flow in the suction bore of the handpiece.

9. A handpiece comprising:

a housing including a suction bore therein;

a coupling assembly disposed at a distal end of the housing;

a motor disposed in the housing;

a sensor for sensing fluid flow or pressure in a suction path and providing a sensor output; a cutting accessory coupled by the coupling assembly to the housing of said handpiece, said cutting accessory comprising a fixed element with an opening and a driven element with an opening that is driven by the motor, the openings defining a window for at least partially opening and closing for providing a fluid path from an exterior of said cutting accessory during movement of the driven element; and a controller for determining movement and position of the driven element relative to the fixed element of the cutting accessory from the sensor output and for controlling the motor for stopping the driven element in a predetermined position.

10. The handpiece of claim 9, wherein the sensor senses pressure in the suction bore.

11. The handpiece of claim 9, comprising an actuator for providing an actuator output to said controller, wherein said controller is disposed in the housing and wherein the sensor comprises a pressure sensor for providing the sensor output.

12. The handpiece of claim 9, comprising an actuator for providing an actuator output to said controller, and wherein the sensor comprises a flow sensor for measuring fluid flow through the suction bore, wherein said controller receives the actuator output and the sensor output to control the motor and operate said cutting accessory at an optimal speed for maximizing cutting by the handpiece.

13. The handpiece of claim 9, wherein the controller is configured to stop the driven element at a predetermined position whereat a window is partially open.

14. A surgical system comprising:

an elongate handpiece comprising a housing with a motor disposed therein, the handpiece including a suction bore;

a suction tube connected to said suction bore at the proximal end of said handpiece;

a cutting accessory having a proximal end coupled at a distal end of said handpiece, said cutting accessory comprising a fixed element and a driven element driven by the motor, wherein during operation of said driven element a window opening defined by openings in the fixed element and the driven element periodically at least partially opens and closes for providing a fluid path from an exterior of said cutting accessory, and through a suction channel of said cutting accessory to said suction bore, wherein said suction tube, said suction bore and the suction channel comprise a suction path;

at least one of a pressure sensor and a flow sensor for providing a signal output;

an actuator for providing an actuator output to power the cutting accessory; and a controller for receiving the signal output and the actuator output, wherein the controller operates the motor to power the cutting accessory at a desired speed corresponding to a predetermined optimal fluid flow rate through the suction bore in response to the signal output and the actuator output, and determines the position of the driven element relative to the fixed element of the cutting accessory from the sensor output by sensing at least one of pressure and fluid flow in the suction path.

15. The surgical system of claim 14, wherein the controller is configured so that during stopping of said motor, said motor drives said driven element to a predetermined position relative to said fixed element to provide a predetermined partially open dimension for the window opening when the motor is stopped.

16. The surgical system of claim 14, wherein the controller is configured to control the motor during stopping of the motor to locate the driven element in a predetermined stopped position with respect to the fixed element resulting in the window between the driven element and the fixed element being closed so that essentially no fluid path opening is provided from the exterior of the cutting accessory to the suction channel.

17. The surgical system of claim 14, wherein said sensor comprises the pressure sensor, and wherein said pressure sensor is disposed in said handpiece for detecting pressure in the suction bore.

18. The surgical system of claim 17, wherein said controller is disposed within said handpiece.

19. The surgical system of claim 18, wherein said actuator is disposed on said handpiece.

20. The surgical system of claim 14, wherein said sensor comprises the flow sensor, and wherein the flow sensor is disposed in said handpiece and in fluid communication with said suction bore.

21. The surgical system of claim 20, wherein said actuator comprises a foot switch.

22. The surgical system of claim 14, wherein said sensor comprises the flow sensor for sensing fluid flow through said suction path.

23. The surgical system of claim 22, wherein said flow sensor comprises one of an ultrasonic flow sensor and an optical flow sensor disposed in said housing.

* * * * *

UNITED STATES PATENT AND TRADEMARK OFFICE
CERTIFICATE OF CORRECTION

PATENT NO. : 8,226,677 B2
APPLICATION NO. : 12/589317
DATED : July 24, 2012
INVENTOR(S) : Barry Kauker et al.

Page 1 of 1

It is certified that error appears in the above-identified patent and that said Letters Patent is hereby corrected as shown below:

IN THE CLAIMS:

Column 13, line 53, in Claim 9:
    Please insert a paragraph after the word "output;".

Column 14, line 16, in Claim 13:
    Please replace "a" with --the--.

Signed and Sealed this
Twentieth Day of November, 2012

David J. Kappos
*Director of the United States Patent and Trademark Office*